United States Patent
Marissen et al.

(10) Patent No.: US 7,582,088 B2
(45) Date of Patent: Sep. 1, 2009

(54) BONE FIXING DEVICE

(75) Inventors: Roelof Marissen, Born (NL); Karel Jozef Wetzels, Kerkrade (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/544,102

(22) PCT Filed: Feb. 6, 2004

(86) PCT No.: PCT/NL2004/000086

§ 371 (c)(1),
(2), (4) Date: Feb. 23, 2006

(87) PCT Pub. No.: WO2004/069068

PCT Pub. Date: Aug. 19, 2004

(65) Prior Publication Data

US 2006/0135958 A1   Jun. 22, 2006

Related U.S. Application Data

(60) Provisional application No. 60/445,464, filed on Feb. 7, 2003.

(30) Foreign Application Priority Data

Feb. 7, 2003   (EP)   ................................... 03075381

(51) Int. Cl.
*A61B 17/82* (2006.01)
(52) U.S. Cl. ........................................................ 606/74
(58) Field of Classification Search ................ 606/74
See application file for complete search history.

(56) References Cited

U.S. PATENT DOCUMENTS 2,502,902 A * 4/1950 Tofflemire ................... 606/54
4,655,203 A * 4/1987 Tormala et al. ............... 606/69

(Continued)

FOREIGN PATENT DOCUMENTS

EP   0 597 257   5/1994

(Continued)

OTHER PUBLICATIONS

International Search Report.

*Primary Examiner*—Eduardo C Robert
*Assistant Examiner*—Jerry Cumberledge
(74) *Attorney, Agent, or Firm*—Nixon & Vanderhye P.C.

(57) ABSTRACT

Bone fixing devices include (I) a surgical cable having a first end and a second end and (II) at least a first fixing plate and a second fixing plate. The first and second fixing plates are respectively provided with first and second central holes and first and second rings surrounding the first and second holes. The circumference of each fixing plate defines an outer edge of its respective ring and an inner edge of the ring being adjacent to the hole it surrounds. The first fixing plate is in a stacked position on top of the second plate so as to define a gap therebetween with the plates and the holes at least partly overlapping each other. The cable ends follow a continuous trajectory running around and between the plates and through the holes in such way that by drawing the cable ends the cable is tensioned around the bone parts so as to and fixate the same.

11 Claims, 3 Drawing Sheets

U.S. PATENT DOCUMENTS

| | | | |
|---|---|---|---|
| 5,376,126 A * | 12/1994 | Lin | 623/23.11 |
| 5,665,089 A | 9/1997 | Dall et al. | |
| 6,045,551 A * | 4/2000 | Bonutti | 606/60 |
| 6,106,545 A | 8/2000 | Egan | |
| 6,231,592 B1 | 5/2001 | Bonutti et al. | |
| 7,094,251 B2 * | 8/2006 | Bonutti et al. | 606/232 |

FOREIGN PATENT DOCUMENTS

| | | |
|---|---|---|
| FR | 2 822 051 | 9/2002 |

\* cited by examiner

BONE FIXING DEVICE

This application is the US national phase of international application PCT/NL2004/000086 filed 6 Feb. 2004 which designated the U.S. and claims benefit of EP 03075381.8, dated 7 Feb. 2003 and U.S. 60/445,464, dated 7 Feb. 2003, the entire content of which is hereby incorporated by reference.

FIELD OF INVENTION

The invention relates to a method for fixing bone parts by means of a Surgical cable.

BACKGROUND AND SUMMARY OF THE INVENTION

In modern surgery on many occasions there is a need for immobilizing bone parts that have been separated in the course of an operation and have to grow together again or to keep a bone part at a fixed and constant distance and position with respect to another bone part or an orthopedic device such as a splint, further denoted as fixing bone parts. Also in the treatment of bone fractures this need for fixing bone parts that came apart is required for at least the time needed to have the body repair the fracture or for longer times, in many cases even for years.

It is known to wrap a steel cable around the bone parts to be fixed, to bring the cable under the required tension to fix the parts against relative movement, e.g. under load, and to leave it in place at least until the bone parts have grown together and the bone has recovered sufficiently to take up its proper function again, or even permanently to avoid a further operation to remove the cable. The cable is tensioned and fixed by guiding its ends from opposite sides through holes in a metal block, tensioning the cable by exerting a drawing force on the ends and pinching the metal block such that the holes collapse and fix the cable.

The use of steel cables brings about a number of disadvantages. They are prone to fatigue leading to breakage of the composing steel fibers after which the sharp ends stick out into the body. Breakage of the fibers during their application by a surgeon brings the risk of stitching and possible blood contact. Further, steel is a hard material and being tensioned around the bone there is the risk of carving of the steel cable into the bone.

U.S. Pat. No. 5,540,703 teaches to use instead of a metal cable a braided polymeric material cable and to lock the tightened and tensioned cable with non-loosening knots, in order to overcome certain disadvantages of metal cables. High performance, i.e. high strength, high modulus, polyethylene in particular is applied as the polymeric material. Fibers of this type, however, are notorious for their difficulty to be fixed by knots, clamps or other means when they are under tension.

The present invention now seeks to provide a method and means for fixing bone parts by means of a surgical cable of a polymeric material that do not suffer from the disadvantages of the known means and cope with the fixing difficulties related to the application of tensioned high performance fibers.

This goal is achieved according to the invention by providing a bone fixing device comprising (I) a surgical cable having a first and a second end and (II) at least a first and a second fixing plate having a first resp. second central hole and a first resp. second ring surrounding said first resp. second hole, the circumference of each fixing plate forming an outer edge of its ring and an inner edge of its ring being adjacent to the hole it surrounds, the first fixing plate being in a stacked position on top of the second plate leaving a gap between the plates and the holes at least partly overlapping each other, wherein at least one end of the cable follows a continuous trajectory running as part (j) from outside the outer edges underneath the second ring up to the second hole, bending upward into a first upward part (a) running through the second and the first holes, a bend to an outward part (b) running across the first ring in the direction of its outer edge, a downward part (c) outside said outer edge running in a direction opposite to the upward part (a), a part (d) running through the hole of the second ring, part (d) at its one end being connected to a trajectory part (e) running through the gap between the fixing plates and at its other end being connected to a trajectory part (f,g) running underneath the second ring, the other end of the cable also being connected to the fixing plates.

It is understood that the trajectory has been defined in the situation that the plate that is to be in contact with the bone parts is denoted as the second plate and is assumed to be on top of these parts. Other situations will be rotated and/or mirrored situations but in these situations the shape and the order of the parts in the trajectory remain essentially the same although upward and downward may have to be interchanged.

The novel fixing device can be easily applied to keep in place bone parts by applying the cable around the parts to be fixed and drawing the ends of the cable that at the end of the trajectory specified thrust out of the fixing plates. It takes a relatively small force tension the cable by drawing the two ends, which at the same time enlarges the clamping force of the two plates on the cable part that runs between the rings of the plates. This clamping, fixing force has appeared considerably larger than the force exerted by the tension in the cable.

In the method according to the invention a fiber surgical cable having two ends is applied. The fiber is a high performance fiber, preferably a polyethylene fiber having a tensile strength of at least 1.8 GPa and a modulus of at least 60 GPa. Examples of such fibers are various Dyneema grades of DSM High Performance Fibers and various Spectra grades of Honeywell Inc. These fibers have been prepared from high molecular weight polyethylene, in particular polyethylene heaving a weight average molecular weight of at least 2,000,000.

In particular the cable is a bundle of parallel, twisted or braided fibers of the type described above. It may also be a high performance tape having the required strength and modulus. The tape may be a single tape or it may be in the form of a flat braid of high performance fibers. Twisting and braiding are commonly applied techniques in cable production and cables obtained by these common techniques are applicable in the device according to the invention. It should be noted that in constructions of these fibers, e.g. in braids and twisted bundles an efficiency loss occurs, i.e. that the resulting strength of the construction is lower that then the sum of the strengths of the constituting fibers. The efficiency depends on the used braid construction, braiding period and braiders. Braid efficiency may range from 30-70%. Starting from the required strength of the cable in each case the proper combination of initial fiber strength, cable thickness and cable construction can be chosen to obtain a cable having at least that required strength. The forces required to fix bone parts generally range from 500 to 3000 N, depending on the size of the bones to be fixed and the forces exerted on the bone parts. For small bones, like in fingers, smaller forces and thicknesses may be relevant. In general the total thickness of the cable will range from 500 to 30,000 dtex.

The cable must be suited to be positioned around the bone parts and has an oblong shape; in particular the cable is a bundle of parallel, twisted or braided fibers of a length that is sufficient to be laid around the bone parts to be fixed and to be tensioned.

The cable in the described shape of a bundle of fibers has two ends. These ends normally will have been treated to prevent unraveling or splitting of the bundle. The ends can e.g. have been treated with a substance gluing together the fibers, have been molten together or otherwise be prevented from unraveling. In this embodiment the last few centimeters of the bundle to the ends form the end parts. In certain embodiments of the invention one end of the fiber may have been formed into an eye by splicing the end back into the bundle.

The device comprises two fixing plates. Here and hereafter a fixing plate is understood to be a flat or slightly curved piece of a material that can withstand the tensile forces specified herein before that are required in bone fixing and is biocompatible. Examples of suitable materials are reinforced thermoset resins, metals and ceramic material. A material is considered biocompatible if it is tolerated when implanted into the human or animal body without causing pain, inflammation, irritation, and poisoning or other unwanted effects to the human and animal body.

The fixing plate mainly is flat but it may be slightly curved to be in conformity to the bone part it will be in contact with.

Each fixing plate comprises a central hole and a ring surrounding the hole. The central hole preferably encompasses the center of the fixing plate but this center is not necessarily the center of the hole. The hole may be circular, oval, square or rectangular or any other regular shape. The same holds for the outer circumference of the ring surrounding the hole. The shape of the hole and of the outer circumference may be the same or different. An elongated shape is preferred since this appears to lead to an orientation of the rings in which the longer part lies in the direction of the cable. This results in a smooth-shaped construction and also the cable is clamped over the largest possible area, giving an optimal clamping force. The ring has an inner edge adjacent to the hole and an outer edge forming the outer circumference of the ring. Preferably the edges are rounded in order to prevent cutting or stitching effects to the surrounding tissues after being applied into a human or animal body and to prevent total or partial cutting of the surgical cable both during application and afterwards.

The size of the fixing plates is chosen to match both the strength requirements and the size requirements set by the size and shape of the bone part it will be applied to. The ratio of the largest dimension of the hole and the largest width of the ring, i.e. the distance between the inner and the outer edge of the ring may vary over a large range and may lie between 0.3 and 0.9. Generally the thickness will be in the range from 0.5 to 4 mm and the largest dimension of the ring will be in the range of 4 to 30 mm. Thus the fixing plates may have the shape of a chain link on the one end of the scale, in which the hole is relatively large and the ring has a relatively large thickness to width ratio, to the shape of a washer on the other end of the scale, in which the hole is relatively small and the ring has a relatively small thickness-to-width ratio. Preferably the thickness of the plates is not larger than 0.5 times to even lower than 0.1 times the largest width of the ring in order to provide a stable positioning of the plates on top of one another.

The two fixing plates are in a stacked position, leaving a gap between them. The width of this gap initially will be about the thickness of the surgical cable. After the cable has been tensioned the fixing plate will be pressed together by the forces exerted for tensioning thus preventing the cable form slipping loose.

The holes at least partly overlap each other when the plates are stacked in a centered manner. Preferably the two plates are of equal shape and size at least with respect to the parts clamping the cable and also preferably the holes have the same size and position within the plate.

The two plates are connected to the cable in a specific way, resulting in a device that can be easily tensioned and in a tensioned state is capable to retain the tension without the cable sliding back. To achieve this at least one end of the cable has to follow a continuous trajectory running as part (j) from outside the outer edges underneath the second ring up to the second hole, bending upward into a first upward part (a) running through the second and the first holes, a bend to an outward part (b) running across the first ring in the direction of its outer edge, a downward part (c) outside said outer edge running in a direction opposite to the upward part (a), a part (d) running through the hole of the second ring, part (d) at its one end being connected to a trajectory part (e) running through the gap between the fixing plates and at its other end being connected to a trajectory part (f,g) running underneath the second ring, the other end of the cable also being connected to the fixing plates.

In a first preferred embodiment wherein part (c) further runs outside the outer edge of the second ring and is connected to one end of part (d) through trajectory part (e) running underneath the second ring from its outer edge to its hole and the other end of part (d) is immediately connected to part (e) running through the gap between the fixing plates in an outward direction and ending outside the plates in a cable end.

In a second preferred embodiment the trajectory parts are in the order (a), (b), (c), (e), (d), followed by trajectory part (g) running underneath the second ring from the hole to the outer edge and ending outside the plates in a cable end.

In general both ends of the cable may follow one of the trajectories, the two trajectories being the same or different.

If an even higher clamping force is preferred an extra loop may precede the defined trajectory, the extra loop running upwardly through the holes and downwardly along the outer edges of the rings back to the holes after which the defined trajectory starts.

Since the clamping force to a certain extent may hamper further tensioning the cable by the pulling of the ends of the cable in a preferred embodiment only one end of the cable follows the defined trajectory whereas the other end is connected to a tensioning device connected to the fixing plates. Thus after maximally tensioning the cable by drawing the one cable end a further tensioning can be obtained by operating the tensioning device. Such tensioning device may comprise a mechanism as used in a turn buckle, a worm wheel and driving screw combination or two cooperating 45° tooth wheels rotating around mutually perpendicular axes or even a simple screw, screwed in the tensioning device and ending in a hook that can be connected to the other end of the cable by a knot or hooking to an eye at that end. These tensioning devices can be connected to the cable in such a way that only a drawing force is exerted on the cable, resulting in its shortening and tensioning but also in such a way that, instead of or next to the drawing force, also a twisting force is exerted the cable, also resulting in further tensioning the cable. When such a device is used the other end of the cable may be knotted to e.g. a hook of the tensioning device but preferably the other end of the cable contains an eye made e.g. by a split or any other non-slipping means for connecting it to the tensioning device.

The invention further relates to a method for fixing bone parts comprising the steps of applying a bone fixing device wherein the two cable ends follow a trajectory as described here before around the bone parts to be fixed, followed by drawing the ends of the cable to tension the cable around the bone parts to the tension required to fix the bone parts.

In a preferred embodiment of this method a bar is inserted between the fixing plates before the cable is tensioned and is removed after the cable has been tensioned. This embodiment has the advantage that the clamping force only works after the bar has been removed and is not hampering the tensioning of the cable before. The thickness of the bar can be small but to have the full benefit of its presence it is preferably at least equal to the thickness of the cable. Since the removal of the bar may lead to a minimal elongation of the tensioned part of the cable the bar should be thin, preferably no more than 10 and more preferably no more than 5 or even 2 mm.

In another embodiment the invention relates to a method for fixing bone parts comprising the steps of applying around the bone parts to be fixed a bone fixing device wherein one end of the cable follows a trajectory as described here before and the other end is fixed to a tensioning device that is connected to the fixing rings 5, followed by drawing said one end of the cable to tension the cable around the bone, removing the slack in the cable, and then tensioning the cable to the tension required to fix the bone parts by operating the tensioning device.

From the drawings the information can be taken as how to lead the cable along the proper trajectory around the fixing plates.

The various embodiments and methods described are not only suitable for the fixing of bone parts but they are also useful for the connection of bones to artificial elements providing some orthotic function, e.g. a splint.

The invention also relates to essential parts of the bone fixing device, in particular the invention further relates to a set of at least two fixing plates and a surgical cable, to a surgical cable and to a ring, prepared or fitted for constructing a bone fixing device according to the invention or prepared for application in the method of the invention.

BRIEF DESCRIPTION OF THE DRAWINGS

The invention will be further illustrated by the following drawings, of which

DETAILED DESCRIPTION OF THE PREFERRED EMBODIMENTS

Figure 1:
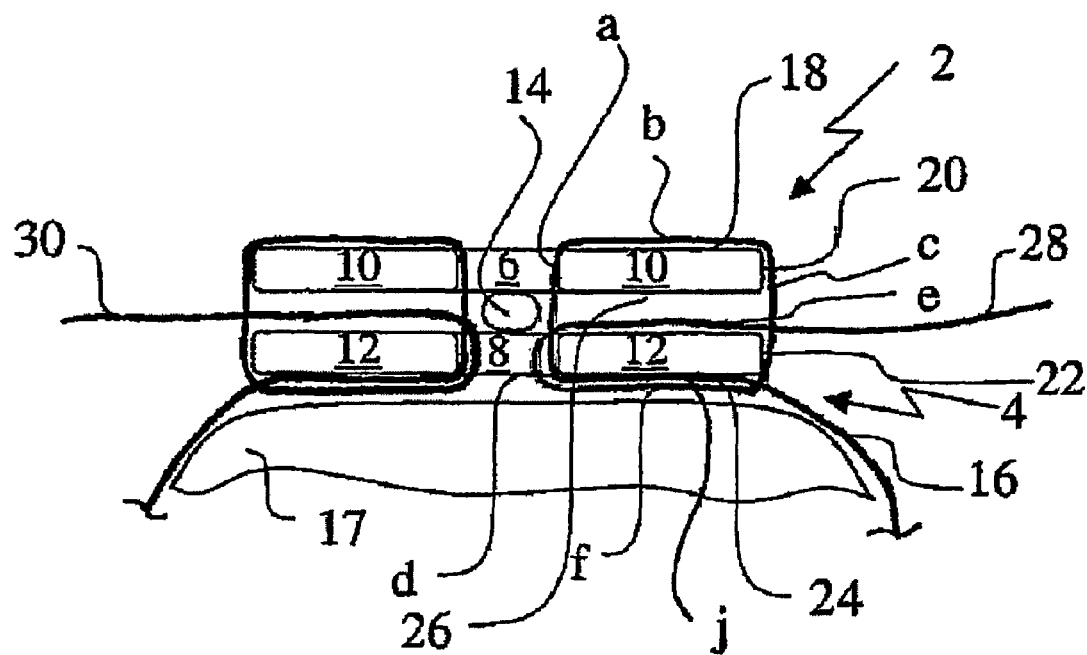
FIG. 1 is a schematic side view of a first embodiment of the bone-fixing device according to the invention.

In FIG. 1 the numbers 2 and 4 denote round fixing plates having a hole 6 resp. 8 surrounded by a ring 10 resp. 12. Between the fixing plates a removable bar 14 is present, Cable 16 surrounds bone parts 17 (not fully shown). One end of cable 16 runs along the trajectory in which parts (a) to (f) are distinguished. Herein part (a) runs upward from below through the holes 8 and 6, then bends to the right in an outward direction and runs as part (b) along the upper surface 18 of the ring 10 to the outer edge thereof, where it bends downward to run as part (c) along the outer circumference 20 and 22 of the rings 10 and 12. The cable then bends to the left in an inward direction and runs as part (f) along the lower surface 24 of ring 12 to the inner edge of this ring, where it bends upward to run as part (d) through hole 8 in plate 4. Finally the cable runs as part (e) through the gap 26 in outward direction bringing end 28 out of the gap. The other end of cable 16 follows a similar trajectory but reversed with respect to center of the holes. The ends 28 and 30 can be grabbed and handled to be drawn and tension the cable 16 around bone parts to keep these fixed with respect to each other. Bar 14 prevents the cable from being clamped already and hampering the tensioning of cable 16.

Figure 2:
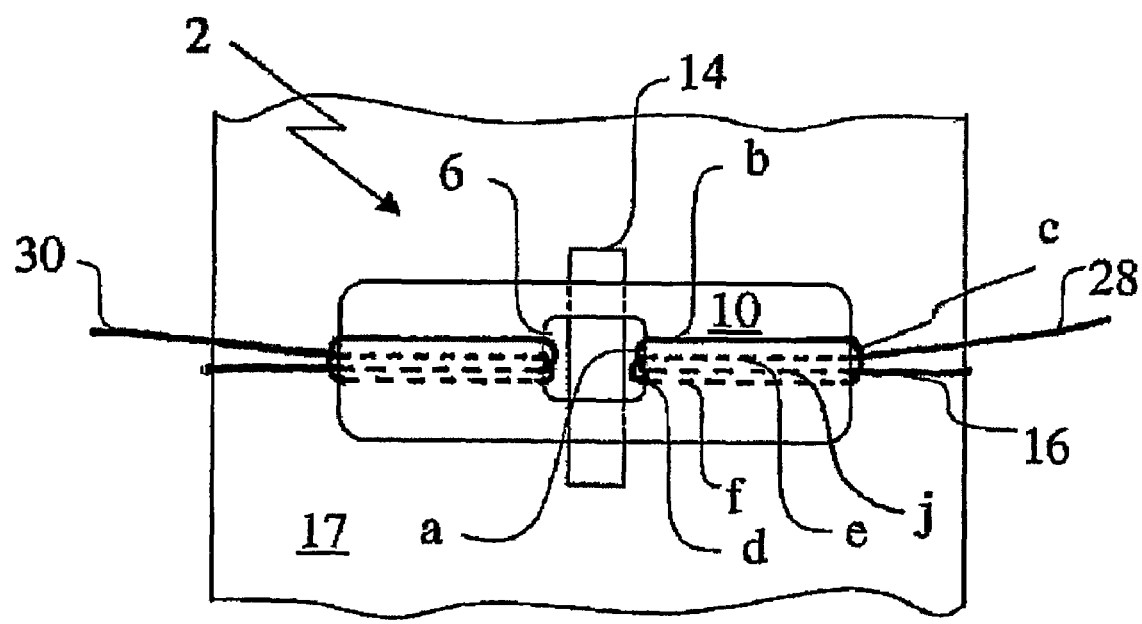
FIG. 2 is a top view of said first embodiment.

In FIG. 2. a top view of the embodiment of FIG. 1 is shown. Bar 14 can be seen through hole 6 in plate 2.

Figure 3:
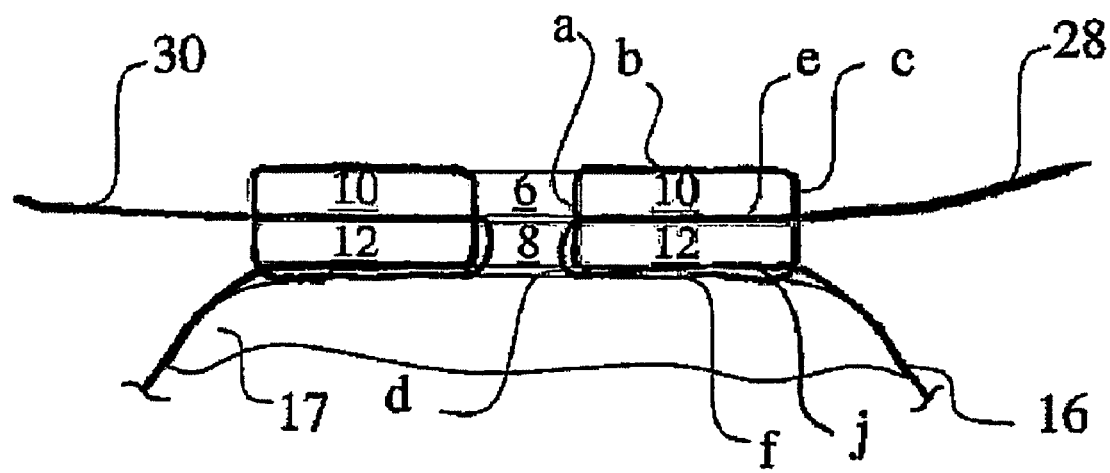
FIG. 3 is a schematic side view of the first embodiment in the tensioned state.
Figure 4:
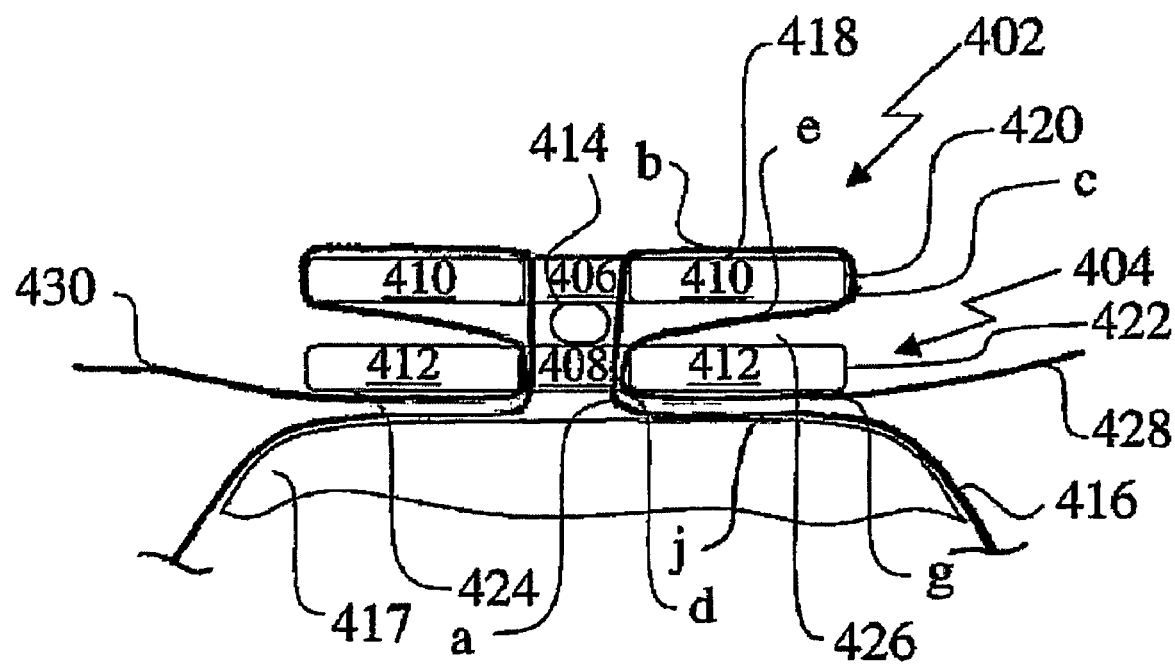
FIG. 4 is a schematic side view of a second embodiment of such a bone-fixing device.

In FIG. 3 bar 14 has been removed and the plates are pressed together by the cable surrounding the plates. The cable is secured from slipping back by the pressure exerted by the plates on the cable at (e), gap 26 being closed now. In FIG. 4 the same two plates in the same relative configuration as in FIG. 1 are present.

In FIG. 4 the numbers of corresponding items have been raised by 400, so 402 is the same item as 2 in FIG. 1 etc. One end of cable 416 runs along the trajectory in which parts (a) to (g) ((f) excluded) can be distinguished. Herein part (a) runs upward from below through the holes 408 and 406, then bends to the right in an outward direction and runs as part (b) along the upper surface 418 of the ring 410 to the outer edge thereof, where it bends downward to run as part (c) along the outer circumference 420 of ring 410. The cable then bends to the left in an inward direction and runs as part (e) through the gap 426 until it reaches the part of the gap between the holes where it bends downward to run as part (d) through hole 408 in plate 404. Finally the cable runs as part (g) in outward direction underneath lower surface 424 of ring 404 bringing end 428 out of the gap. The other end of cable 416 follows a similar trajectory but reversed with respect to center of the holes. The ends 428 and 430 can be grabbed and handled to be drawn and tension the cable 416 around bone parts 417 to keep these fixed with respect to each other. Bar 14 prevents the cable from being clamped already and hampering the tensioning of cable 16.

Figure 5:
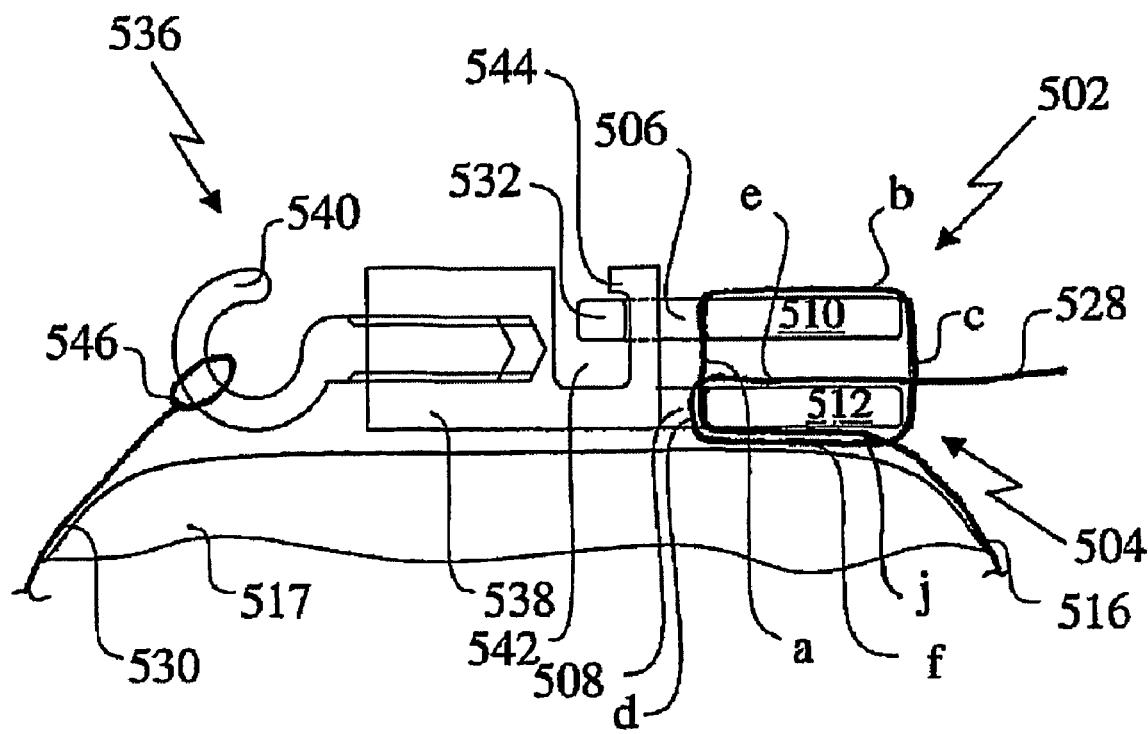
FIG. 5 is a schematic side view of a third embodiment of such a bone-fixing device.

In FIG. 5 502 and 504 are two asymmetric fixing plates having holes 506 and 508 respectively The ring around each hole has a first part 510 resp. 512 the surface area of which is large enough to give sufficient clamping force on a cable following a trajectory as described before. In this FIG. 5 one end of the cable follows the trajectory described under FIG. 1. The part 532 resp. 534 of the rings at the opposite side of the hole with respect to the first part is smaller that the first part. A tensioning device 536 consists of a first part 538 in which a longitudinal bore is present provided with internal screw thread in which a hook 540 is mounted. The other end 530 of the cable has an eye 546 to which the hook 540 has been attached. The tensioning device 536 further consists of a second part that consists essentially of a recess 542 extending from about the center of the device to its end opposite of the side where the bore is present and extending over its full width. The recess ends at a wall 544. The thickness of this wall is such that it fits in the hole of the plates, leaving sufficient room for the cable to be guided through the holes along the clamping trajectory. Lower plate 504 forms part of the tensioning device. Plate 502 can move upward and downward with respect to plate 504. The bottom 544 of recess 542 is at the same level as the surface of plate 504. This allows ring 510 to be in contact over its complete surface area with ring part 512 of the lower plate when plate 502 is pressed downward when drawing on cable end 528 tensions the cable. Plate 502 is mounted on the tensioning device such that the wall 544 extends through hole 506. Turning hook 540 in a counter clockwise direction tensions the cable further.

Further, also in this embodiment a bar can be inserted between the rings during the tensioning and then removed when the desired tension is applied.

Figure 6:
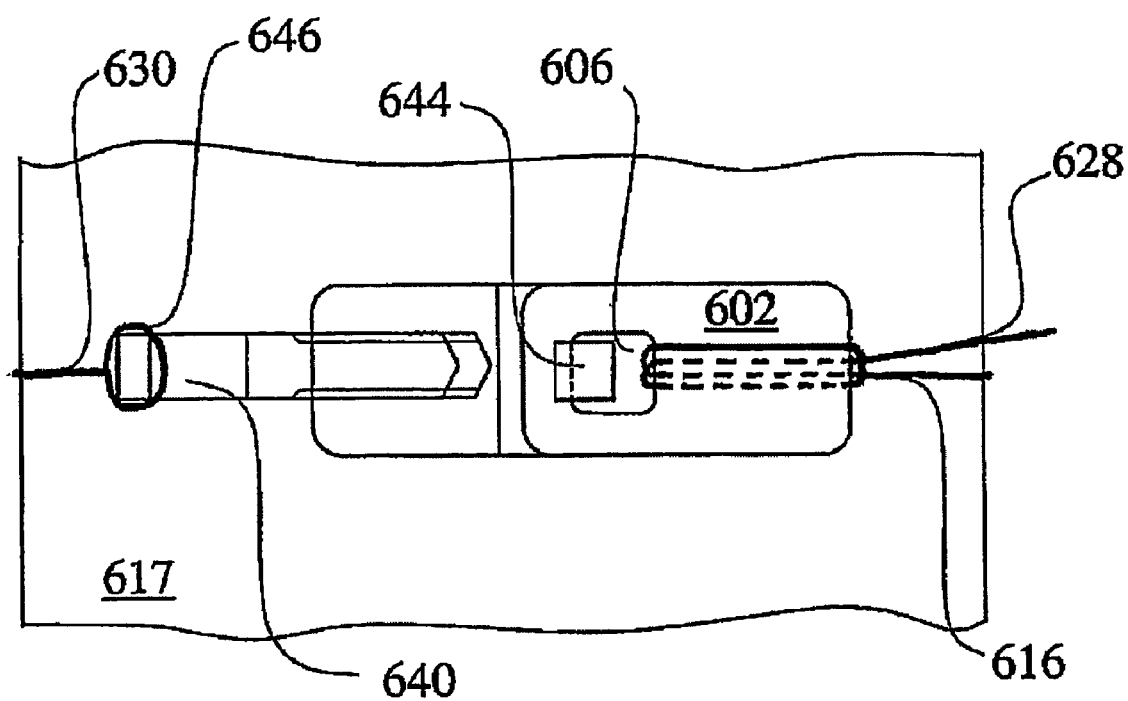
FIG. 6 is a top view of said third embodiment.

In FIG. 6 in hole 606 of top plate 602 the top of wall 644 sticking through said hole, is visible. Cable end 630 with eye 646 is connected to hook 640.

The invention claimed is:

1. Bone fixing device comprising:
   (I) a surgical cable having a first end and a second end, and
   (II) at least a first fixing plate and a second fixing plate respectively having first and second central holes and first and second rings surrounding said first and second holes, wherein each of the first and second fixing plates has an outer edge defining an outer circumference thereof and an inner edge defining a respective one of the first and second central holes,
   the second fixing plate being positionable into contact with a bone part to be fixed and the first fixing plate being in a stacked position on top of the second fixing plate when positioned against the bone part to be fixed so as to establish a gap therebetween such that the first and second central holes at least partly overlap each other, wherein
   each of the first and second ends of the cable is connected to the first and second fixing plates, and wherein
   at least one of the first and second ends of the cable follows a continuous trajectory having sequential trajectory parts comprising an initial trajectory part (j) running from outside the outer edges underneath the second ring and up to the second hole, the at least one end of the cable thereafter bending upward into a first upward trajectory part (a) running through the second and the first holes, respectively, bending to an outward trajectory part (b) running across the first ring in a direction from its inner edge toward its outer edge, bending to a downward trajectory part (c) outside at least the outer edge of the first ring running in a direction opposite to the first upward trajectory part (a), bending to an inner trajectory part (d) running through the second central hole of the second ring, wherein the inner trajectory part (d) includes one and other ends, the one end thereof being connected to a first radial trajectory part (e) running through the gap established between the first and second fixing plates and the other end thereof being connected to a second radial trajectory part (f) running underneath the second ring.

2. Device according to claim 1, wherein the downward trajectory part (c) further runs outside the outer edge of the second ring and is connected to the other end of the inner part through the second radial trajectory part (f) running underneath the second ring from its outer edge to the second central hole, and wherein the one end of the inner part is immediately connected to the first radial trajectory part (e) running through the gap established between the first and second fixing plates in an outward direction and ending outside the plates as a cable end.

3. Device according to claim 1, wherein the first upward trajectory part (a), the outward trajectory part (b), the downward trajectory part (c), the inner trajectory part (d) and the first radial trajectory part (e) are arranged sequentially in order in the continuous trajectory of the cable followed by the second radial trajectory part (f) which runs underneath the second ring in a direction from the second central hole to the outer edge thereof and ends outside the first and second fixing plates as a cable.

4. Device according to claim 1, wherein each of the first and second ends of the cable follow the continuous trajectory.

5. Device according to claim 1, further comprising a tensioning device connected to the first and second fixing rings, wherein the other of the first and second ends of the cable is fixed to the tensioning device.

6. Method for fixing bone parts comprising the sequential steps of positioning a bone fixing device according to claim 1 relative to the bone parts to be fixed such that the second fixing plate is positioned in contact with the bone parts to be fixed and the first fixing plate is in a stacked position on top of the second fixing plate, followed by drawing the first and second ends of the cable to tension the cable around the bone parts to the tension required to fix the bone parts.

7. Method according to claim 6, further comprising inserting a bar between the first and second fixing plates before the cable is tensioned and thereafter removing the bar after the cable has been tensioned.

8. Method for fixing bone parts comprising the steps of applying a bone fixing device according to claim 5 around the bone parts to be fixed, followed by drawing said one end of the cable to tension the cable around the bone and then tensioning the cable to the tension required to fix the bone parts by means of the tensioning device.

9. Device according to claim 1, wherein the first and second holes each encompass a center of the first and second rings, respectively.

10. Device according to claim 9, wherein the center of the first and second rings corresponds to a center of the first and second central holes, respectively.

11. Device according to claim 9, wherein the first and second holes are circular, oval, square, rectangular or other regular shape.

* * * * *